United States Patent [19]

Harrison et al.

[11] Patent Number: 5,306,631
[45] Date of Patent: Apr. 26, 1994

[54] COMPOSITIONS AND METHOD FOR INHIBITION OF HIV PRODUCTION

[75] Inventors: Gail Harrison; Ian H. Maxwell; Francoise Maxwell, all of Denver; L. Michael Glode, Aurora, all of Colo.

[73] Assignee: University of Colorado Foundation, Inc., Boulder, Colo.

[21] Appl. No.: 685,601

[22] Filed: Apr. 15, 1991

Related U.S. Application Data

[63] Continuation-in-part of Ser. No. 88,086, Aug. 21, 1987, abandoned.

[51] Int. Cl.$^5$ .................. C12N 15/00; C12N 5/00
[52] U.S. Cl. .................. 435/172.3; 435/240.2; 435/320.1; 935/56; 935/71
[58] Field of Search ............. 435/172.3, 320.1, 317.1, 435/948, 240.2, 69.7; 536/27; 935/27, 32, 57, 71, 111, 71.56

[56] References Cited

U.S. PATENT DOCUMENTS

4,867,976 9/1989 Ueda et al.

FOREIGN PATENT DOCUMENTS

9007936 7/1990 PCT Int'l Appl.

OTHER PUBLICATIONS

Maxwell et al., (a) J. Cell. Biochem. 0(11 Part D): 67 Abstract #p. 314 (1987).
Maxwell et al. (b), J. Cell Biochem. 0(10 Part D): 39, Abstract #N93 (Published Mar. 31, 1986).
Leong et al., Science 220: 515–517 (1983).
Schwartz et al., Gene 88: 197–205 (1990).
Palmiter et al. (1987) Cell 50:435–443.
Baltimore et al. (1988) Nature 335:395–396.
Maxwell et al. (1986) Cancer Res. 46:5660–4664.
Chaudary et al. (1988) Nature 335:369–372.
Breitman et al. (1990) Mol. Cell. Biol. 10 (2):474–479.
Yamaizumi et al. (1978) Cell 15:245–250.
Miller et al. (1989) BioTechniques 7(9):980–990.
Uchida et al. (1973) J. Biol. Chem. 248(11):3838–3844.
Maxwell et al. (1987) Mol. Cell. Biol. 7(4):1576–1579.
Maxwell et al. (1989) BioTechniques 7(3):276–280.
Cochrane et al. (1990) PNAS USA 87:1198–1202.
Rosen et al. (1988) PNAS USA 85:2071–2075.
Hadzopoulou-Cladaras et al. (1989) J. virol. 63(3):1265–1274.
deWet et al., (1987) Mol. Cell. Biol. 7(2): 725–737.
Nabel et al. (1987) Nature 326:711–713.
Garcia et al. (1989) The EMBO J. 8(3):765–778.
Venkatesh et al. (1990) PNAS USA 87:8746–8750.
Gilboa et al., (1986) BioTechniques 4(6):504–512.
Armentano et al., (1987) J. Virol. 61(5):1647–1650.
Maxwell et al. (1990) J. Cell. Biochem. Suppl. 0(14 part D):107.
Harrison et al. (1989) J. Cell. Biochem. 0(13 part B): 302.
Felber et al. (1988) Science 239:184–187.
Rosen et al. (1985) Cell 41:813–823.

*Primary Examiner*—Jasemine C. Chambers
*Attorney, Agent, or Firm*—Greenlee & Winner

[57] ABSTRACT

A method for the selective killing of HIV-infected cells, via HIV-regulated expression of a toxin gene, is provided in the present invention. Specifically, the expression of the diphtheria toxin fragment A gene is subject to tight control by cis-acting HIV regulatory sequences and trans-acting regulatory factors. Also provided is a method of protecting a host from HIV infection by the stable transformation of target cells, those cells which can be infected with HIV, with an HIV-regulated toxin gene. When such a stably transformed cell becomes infected with HIV, induction of the toxin gene prevents the replication and spread of the virus.

14 Claims, 6 Drawing Sheets

FIG. 5A
1  2  3  4  5  6  7  8  9
1  2  3  4  5  6  7  8  9  10  11  12
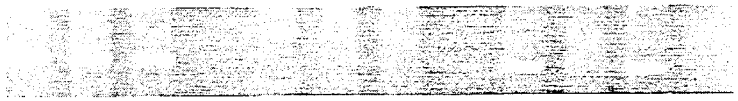
FIG. 5B

COMPOSITIONS AND METHOD FOR INHIBITION OF HIV PRODUCTION

This work was supported at least in part by funding from the National Institutes of Health (NIH). The United States government has certain rights in this invention.

CROSS-REFERENCE TO RELATED APPLICATIONS

This application is a continuation-in-part of U.S. Ser. No. 07/088,086, filed Aug. 21, 1987, now abandoned which is in its entirety, incorporated by reference herein.

FIELD OF THE INVENTION

The present invention provides a novel approach to achieve selective lethality of target cells. This approach involves the selective expression within the target cells of active toxin from chimeric toxin genes. Specifically, a toxin coding sequence is expressed under the regulatory control of HIV cis-acting nucleotide sequences and HIV trans-acting factors.

BACKGROUND OF THE INVENTION

The present invention is based on the surprising discovery that the diphtheria toxin fragment A can be selectively targeted to certain mammalian cell types by introduction into the cell of chimeric toxin genes in which expression of a toxin fragment A coding sequence is controlled by mammalian cell-specific regulatory sequences. The toxin fragment A coding sequence was selectively expressed in the target mammalian cell, inhibiting protein synthesis and resulting in cell death. Cell-specific expression of such chimeric toxin genes was sufficiently restricted to effect selective killing of targeted cells without elimination of non-targeted cells. It was surprising that selective lethality could be obtained using such chimeric toxin genes because there was evidence that the introduction of a single molecule of fragment A into a cell would be lethal (Yamaizumi et al. (1978) Cell 15:245–250) and it was not known, prior to the present invention, if cell-specific regulation, particularly of heterologous coding regions, would be restricted enough to cause selective lethality.

Attempts have been made to use the diphtheria toxin A fragment to selectively kill undesirable cells, such as malignant cells, without destroying healthy cells. Such attempts have concentrated on replacement of the natural fragment B protein delivery mechanism with alternate delivery mechanisms based on the specificity of certain proteins for cell surface molecules, for example by preparing toxin fragment A protein conjugates with antibodies (immunotoxins), hormones or plant lectins.

Diphtheria toxin is synthesized and secreted by strains of *Corynebacterium diphtheriae* which are lysogenic for bacteriophage $\beta^{tox+}$. The naturally occurring toxin is a single polypeptide of about 58 kd (535 amino acids) which is highly toxic to many animal species. Diphtheria toxin inhibits protein synthesis in and is toxic to most eukaryotic cells that have been tested. The toxin is composed of two regions, separable by proteolytic cleavage, which are functionally distinct. Toxin activity is associated only with fragment A, the $NH_2$-terminal region of 193 amino acids. Fragment A functions by catalyzing the inactivation of elongation factor-2 (EF-2). The COOH-terminal 342 amino acid fragment B, is itself non-toxic, but functions to deliver the toxin fragment A to cells. Fragment A is non-toxic unless it is introduced into the cell cytoplasm. Purified toxin fragment A has been demonstrated to be highly toxic when introduced artificially into cells. A review of the structure and function of diphtheria toxin is provided in Pappenheimer (1977) Ann. Rev. Biochem. 46:69–94.

The diphtheria toxin (DT) gene, tox, is located on bacteriophage $\beta$. The entire gene has been cloned and sequenced by separately cloning fragments having little or no toxic activity (Greenfield et al. (1983) Proc. Natl. Acad. Sci. USA 80:6853–6857). Several non-toxic mutant tox genes have also been cloned including tox45 (Leong et al. (1983) Science 220:515–517) which has a wild-type region A and non-functional B region, and tox228 (Kaczorek et al. (1983) Science 221:855–858) which carries mutations in both the A and B regions. Uchida et al. (1973) J. Biol. Chem. 248:3838–3844 and ibid. pp. 3845–3850 have identified several mutant DT proteins, designated CRM's (cross-reacting materials) which are non-toxic (CRM45, 197, 228) or have reduced toxicity (CRM176). The attenuated toxicity (about 90% of wild-type) of CRM176 results from a mutation in the A region which affects enzymatic activity of the tox176 fragment A. The coding sequence of the mature toxin is preceded by a signal sequence which presumably functions in secretion of tox gene product (Kaczorek et al. (1983)).

It is known that many differentiated eukaryotic cells synthesize proteins that are unique to a particular cell type. For example, it has been demonstrated that immunoglobulin kappa is specifically expressed in B lymphocyte cells, that interleukin-2 is selectively expressed in activated T-cells (Fujita et al. (1986) Cell 46:401–407), that gamma 2-crystallin is specifically expressed in the fiber cells of the ocular lens (i.e., Breitman et al. (1984) Proc. Natl. Acad. Sci. USA 81:7762), that elastase I is specifically expressed in pancreatic acinar cells (Ornitz et al. (1985) Nature 313:600–602), that insulin is specifically expressed in pancreatic endocrine $\beta$-cells, and that chymotrypsin is specifically expressed in pancreatic exocrine cells (Walker et al. (1983) Nature 306:557–561). Additionally, there are examples of non-specific but preferential expression of transferrin (McKnight et al. (1983) Cell 34:335–341) and metallothionein in the liver. A particularly important type of cell-preferential expression occurs with certain retroviruses including human T-cell leukemia viruses, HTLV's (Sodroski et al. (1984) Science 225:381–385; Sodroski et al. (1985) ibid. 227:171–173) and bovine leukemia virus, BLV (Derse et al. (1985) Science 227:317–320; Rosen et al. (1985) ibid. 227:320–322). Markedly enhanced viral expression is observed in cells already infected with the virus. Selective transcription is stimulated by trans-acting regulatory factors produced in infected cells. These stimulatory factors appear to be unique for each virus. Sequences associated with control of stimulated expression have been localized to the long terminal repeat (LTR) sequence of both HTLV's and BLV. Heterologous genes placed under control of the LTR sequences are reported to be preferentially expressed in infected cells.

Chimeric genes in which a heterologous mammalian or viral structural gene is placed under the control of cell-specific regulatory elements have been reported to be successfully expressed in a cell-specific manner. An elastase-human growth hormone gene fusion was shown to be specifically expressed in pancreatic acinar cells of transgenic mice (Ornitz et al. (1985) supra). Oncogenes placed under the control of elastase and gamma A crystallin gene regulatory sequences have been shown to be specifically expressed (i.e., induce tumors) in the pancreas and ocular lens, respectively of transgenic mice (Ornitz et al. (1985) Cold Spring Harbor Symp. Quant. Biol. 50:389-409; Quaife et al. (1987) Cell 48:1023-1034; Mahon et al. (1987) Science 235:1622-1628).

A number of bacterial genes have been successfully expressed in mammalian cells under the control of mammalian promoters and regulatory sequences (see, for example, Gorman et al. (1982) Mol. Cell. Biol. 2:1044-1051; Southern and Berg (1982) J. Mol. Appl. Genet. 1:327-341). In fact, bacterial genes such as chloramphenicol acetyl transferase (CAT), aminoglycoside 3' phosphotransferase (neo), guanine phosphoribosyl transferase (gpt) and $\beta$-galactosidase (lacZ) are often used as detectable or selectable markers in the study of mammalian expression systems. For example, the bacterial $\beta$-galactosidase gene has been used to assess heat shock expression in Drosophila (Lis et al. (1983) Cell 35:403-410) and tissue-specific expression mediated by the gamma 2-crystallin promoter in the ocular lens of transgenic mice (Goring et al. (1987) Science 235:456-458).

Specific DNA sequences which function in cell-specific regulation have been isolated and identified in many cases. In most systems that have been studied, cell-specific expression is mediated by an enhancer, a cis-acting DNA sequence, which is believed to selectively activate expression in a target cell in response to tissue or cell-specific trans-acting factors. Immunoglobulin heavy chain (IgH) enhancers are selectively active in B-cells and are among the best characterized cell-specific expression elements (Gillies et al. (1983) Cell 33:717-728; Picard and Shaffner (1984) Nature 307:80-82; Ephrussi et al. (1985) Science 227:134-140). Enhancers are also reported to function in cell-selective expression of elastase (Hammer et al. (1987) Mol. Cell. Biol. 7:2956-2967), insulin (Edlund et al. (1985) 230:912-916) and interleukin-2 (Fujita et al. (1986)). It has recently been reported that cell-type specificity of immunoglobulin genes is conferred not only by the IgH enhancer but also by a 5'-upstream element associated with an immunoglobulin gene promoter (Mason et al. (1985) Cell 41:479-487; Foster et al. (1985) Nature 315:423-425). This upstream element apparently confers a level of cell-selective expression independent of the heavy chain enhancer. A similar 5'-upstream promoter associated element is reported to function in insulin gene regulation (Edlund et al. (1985)). In contrast, no such promoter associated element is believed to function in interleukin-2 regulation (Fujita et al. (1986)).

It has been reported (Maxwell et al. (1986) Cancer Research 46:4660-4664, which is incorporated by reference herein) that the diphtheria toxin A-chain (DT-A) gene is regulated in a cell-specific manner on transfection into human cells. This reference also reported selective killing of B-cells caused by expression of DT-A under the control of the immunoglobulin heavy chain enhancer. This reference also suggests that cell-specific regulatory mechanisms can be employed generally for selective cell killing by expression of a toxin gene and that such selective killing has application to cancer therapy. A second report (Maxwell et al. (1987) Mol. Cell. Biol. 7:1576-1579, which is incorporated by reference herein) describes the cloning and sequencing of the attenuated diphtheria toxin 176 and suggests the use of the tox176 coding region for selective cell killing.

Recently, it has been reported (Palmiter et al. (1987) Cell 50:435-443, which is incorporated by reference herein) that a chimeric diphtheria toxin fragment A coding sequence expressed under the regulatory control of an elastase I enhancer/promoter was selectively expressed in pancreatic acinar cells. Selective expression and selective lethality of the chimeric toxin gene was demonstrated by the production of transgenic mice lacking a normal pancreas. Similar results have also been obtained (Breitman et al. (1987) Science, 238:1553-1555) with diphtheria toxin fragment A under the control of gamma crystallin gene regulatory sequences, resulting in selective elimination of lens tissue in transgenic mice.

Some recently suggested approaches to therapy for Acquired Immune Deficiency Syndrome (AIDS) involve "intracellular immunization", a term coined by Baltimore ((1988) Nature 335:395-396) to describe the genetic modification of cells to render them incapable of supporting viral production. We have been exploring the use of regulated expression of a gene encoding a potent toxin, diphtheria toxin A fragment (DT-A) or an attenuated toxin fragment, to selectively kill cells infected with human immunodeficiency virus (HIV-1).

As described herein, we have placed expression of the reporter gene luciferase (luc), or of DT-A, under control of the HIV-1 trans-acting, essential Tat and Rev proteins. The Tat protein acts on a cis-acting element mapped to region $+14$ to $+44$ (referred to as the TAR region) of the HIV long terminal repeat (LTR) to increase viral expression from the LTR (Arya et al. (1985) Science 229:69-73; Rosen et al. (1985) supra; Sodroski et al. (1985) supra: Green et al. (1989) Cell 58:215-223). The Tat protein appears to exert an effect at both transcriptional (Peterlin et al. (1986) Proc. Natl. Acad. Sci. USA 83:9734-9738; Hauber et al. (1987) Proc. Natl. Acad. Sci. USA 84:6364-6368; Laspia et al. (1989) Cell 59:283-292) and post-transcriptional levels (Cullen (1986) Cell 46:973-982; Feinberg et al. (1986) Cell 46:807-817; Wright et al. (1986) Science 234:988-992; Braddock et al. (1989) Cell 58:269-279; Edery et al. (1989) Cell 56:303-312) and can stimulate expression of heterologous genes placed 3' to the TAR region (Tong-Starksen et al. (1987) Proc. Natl. Acad. Sci. USA 80:6845-6849; Felber and Pavlaskis (1988) Science 239:184-187). The Rev protein relieves the negative regulatory effect of cis-acting repressive sequences (crs) found in the env region of the HIV-1 genome (Rosen et al. (1988) Proc. Natl. Acad. Sci. USA 85:2071-2075; Hadzopoulou-Cladaras et al. (1989) J. Virol. 63:1265-1274) which repress the production of viral unspliced and singly spliced messenger RNAs (mRNAs). The Rev protein acts by binding to RNA at the Rev responsive element (RRE; Malim et al. (1989) Nature 338:254-257; Cochrane et al. (1990) Proc. Natl. Acad. Sci. USA 87:1198-1202), also localized to the env region; binding of the Rev protein to the RRE is essential for Rev function. Rev protein expression results in an increased accumulation of unspliced and singly spliced viral mRNAs, encoding structural proteins, in the cytoplasm (Felber et al. (1989) Proc. Natl. Acad. Sci. USA 86:1495-1499; Zapp and Green (1989) Cell 58:215-223). Thus, expression of the Rev protein promotes the transition from early or latent infection to productive infection. Like Tat, the Rev protein can also act in trans to activate expression of heterologous genes which contain the negative crs sequences and a correctly oriented RRE (Rosen et al. (1988) supra; Felber et al. (1989) supra). We demonstrate here that efficient regulation of both chimeric luc and chimeric DT-A expression by the Tat and Rev proteins can be achieved in transfected cells in vitro. Such regulation is applicable as a novel approach for treatment of AIDS, exploiting the extreme toxicity of DT-A to kill virus-infected cells.

SUMMARY OF THE INVENTION

It is an object of the present invention to provide a method for the specific (i.e., selective) killing of a particular cell type, in particular cells infected with a pathogenic agent which is characterized as producing trans-acting factors which regulate gene expression. In particular, a method is provided for the selective killing of HIV-infected cells by inducing the expression of a cytotoxic protein gene in response to trans-acting regulatory factors produced during HIV replication. In one embodiment, HIV-infected cells are targeted for selective killing using a recombinant diphtheria toxin A chain gene expressed under the regulatory control of HIV cis-acting sequences from the env region responsive to the Rev protein placed downstream of the toxin coding sequence and sequences from the LTR region responsive to the Tat protein placed upstream of the toxin coding sequence to produce an HIV-regulated chimeric toxin gene. Expression of the chimeric toxin gene is activated by the Tat and Rev proteins of HIV. In a particular embodiment, the upstream cis-acting regulatory sequences are those of nucleotides −167 to +80 of HIV LTR, and the downstream regulatory sequences comprise the crs sequences and the Rev response element (RRE) in the region of nucleotides 5925 to 8608 region of the HIV-1 env gene. The toxin coding sequence is that of the A chain of diphtheria toxin. In a second embodiment a host is protected from HIV infection by the stable transformation of an HIV-regulated toxin gene in target cells which can be infected with HIV. When a stably transformed target cell becomes infected with HIV, then the expression of the toxin gene is induced by the viral Tat and Rev proteins, and the death of that cell results from the lethal intracellular action of the toxin A chain. Cell death will occur before the virus can proliferate, and infection of further cells will be prevented because there will be no progeny virus released. The selectivity in killing target cells entails minimal killing, preferably no killing, of nontarget cells; as specifically exemplified, target cells are infected with HIV and non-target cells are not infected with HIV.

Any means known to the art can be used to stably transform target host cells. For example, liposomes containing recombinant DNA molecules and specific for HIV-infectible cells or HIV-infectible cell-specific recombinant retroviruses containing the HIV-regulated toxin gene can be used to introduce the chimeric toxin gene into host cells. Where it is desired to kill cells already infected with HIV, there is no need for the stable transfection of the host cells. Where it is desired to protect HIV-infectible cells from HIV infection, then it is necessary that the cells be stably transfected with the chimeric toxin gene without the killing of uninfected cells. For this application, it may be desirable to use a DT-A gene which encodes an attenuated toxin A chain to minimize cell death in the absence of inducing HIV. A preferred embodiment of an attenuated DT-A toxin gene is the tox176 sequence. Another preferred embodiment is one in which the regulation of the HIV-regulated chimeric toxin gene is sufficiently tightly down-regulated in the absence of HIV trans-acting factors that lethal amounts of the toxin are not produced. The skilled artisan will know how to select the appropriate toxin coding sequence and the appropriate recombinant nucleic acid molecule and means to introduce it according to the intended use.

Another aspect of the present invention is the use of the combination of recombinant DNA molecules comprising HIV-regulated luciferase and HIV-regulated diphtheria A chain genes in the assay of potentially therapeutic compositions for use in the treatment of AIDS. The dependence of luciferase expression on HIV trans-acting functions and the DT-A-mediated inhibition of luciferase allows the assessment of viral replication as a function of a decrease in luciferase activity. The measurement of protein synthesis in general by any means known to the art will allow the determination that the decrease in protein synthesis is due to DT-A expression rather than to a failure to induce the expression of the luciferase gene. It is further understood that an HIV-regulated luciferase gene can be used in an assay for HIV infection or for the presence of Tat and Rev proteins, with the measurement of luciferase activity or with transcriptional expression of the luciferase coding sequence. The use of either a stably transfected cell line or a transient expression assay will serve for these purposes

BRIEF DESCRIPTION OF THE FIGURES

In FIG. 3 Panel B, which shows trans-activated expression, HeLa cells were co-transfected with 4 μg of pRSVL, and 0.2–0.3 μg of pTHA43 or pTHA44 with or without 1.0–1.5 μg each of pH3tat and/or pH3art (with pTHA42 filler added to a total of either 6.2 or 7.3 μg), and harvested for assays 15–16 hours following electroporation. Luciferase levels are expressed as a percentage of the corresponding control (that obtained with pRSVL+filler pTHA44+the corresponding amounts of the other plasmids). Expression of the results in this way corrected for a slight inhibitory effect of pH3tat on pRSVL expression. Each bar represents an average from four experiments, performed with duplicate samples. Standard deviations are indicated by the error bars.

FIGS. 5A–5B shows the results of PCR amplification of a 330 base pair DT-A sequence from (a) DNA, or (b) RNA (reverse transcribed to cDNA) from pTHA43 positive (43-A2, -C2G, -C21, -D4, -D6) or pTHA43 negative (43-B4, -A5, -C3) clones. Oligonucleotide primers amplified a band of ~330 base pairs corresponding to DT-A sequences. Lanes in FIG. 5 Panel A are: 1, 43-A2; 2, 43-B4; 3, 43-C2G; 4, 43-A5; 5, 43-D6; 6, 43-D4; 7, 43-C3; 8, 43-C21; 9, reagents only.

Lanes in FIG. 5 Panel B are: 1-4, 43-C21; 5-8, 43-C3; 9-12, 43-D4. Cells were either not transfected (lanes 1,5,9); or transfected with 2.5 μg pLUCA43 (2,6,10) or 2.5 μg each of pLUCA43+pH3tat+pH3art (3,4,7,8,11,12). RNA was reverse transcribed for all lanes except 4, 8 and 12, which were mock reverse transcribed with no reverse transcriptase added. The band in lane 10 was only faintly visible.

Figure 6:
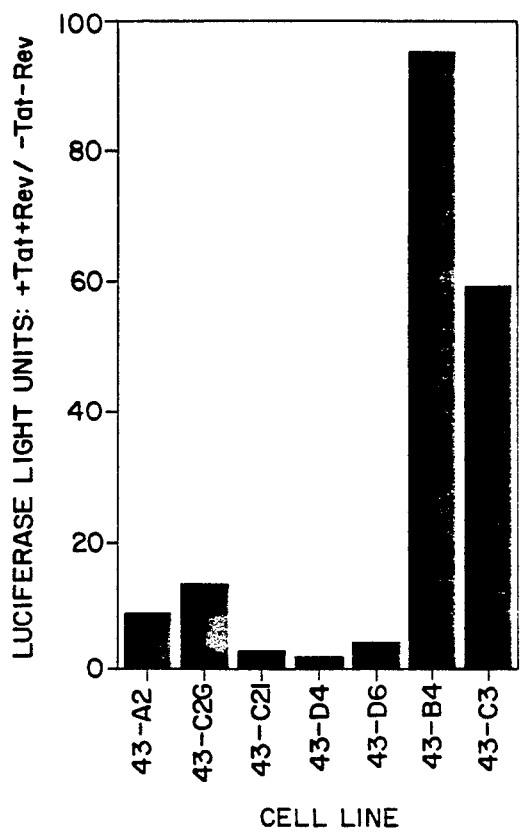

FIG. 6 shows the ratios of induced (electroporated with pLUC43+pH3tat+pH3art) to uninduced light production in five cell lines stably transformed with pTHA43 (43-A2, 43-C2G, 43-C21, 43-D4, 43-D6) and in G418-resistant cell lines lacking the DT-A sequence of pTHA43 (43-B4, 43-C3).

Figure 7:
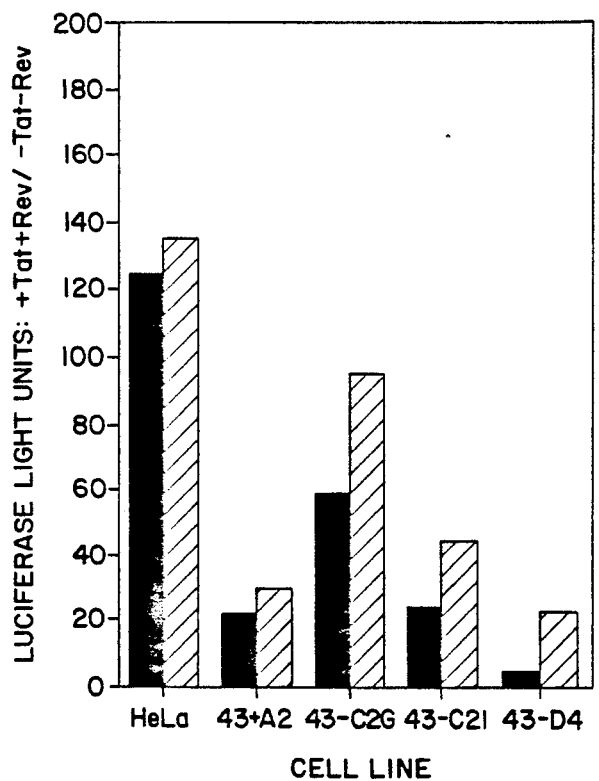

FIG. 7 illustrates the effect of electroporation of DT antitoxin together with pLUC43, pH3tat and pH3art (diagonally hatched bars) as compared to the electroporation of pLUC43, pH3tat and pH3art without DT antitoxin (solid black bars) in HeLa cells and in four cell lines stably transformed with pTHA43.

DETAILED DESCRIPTION OF THE INVENTION

The term "intracellular immunization" has been coined to describe the genetic modification of cells to render them incapable of supporting productive virus infection (Baltimore (1988) supra). This has, for example, been explored by introducing a mutant HIV gag gene into cells by stable transformation, and demonstrating that these cells could not support HIV production (Trono et al. (1989) Cell 59:112–120). We suggest that DT-A is an ideally suited candidate for intracellular immunization, due to its potency and rapid action. Compared with other gene therapy approaches which will generally require sustained expression of substantial amounts of protein, our approach requires only transient expression of small amounts of protein to be effective in killing an HIV-infected cell. Furthermore, when placed under control of the early viral regulatory proteins, regulated DT-A expression should result in cell death before viral production begins; release of progeny virus has been estimated to start about 24 hours after infection in a model system using H9 cells (Kim et al. (1989) J. Virol. 63:3708–3713). Because the methods of the present invention mediate the killing of an HIV-infected cell and substantially prevent the release of progeny virus, the spread of infection within a patient is prevented. Thus, if the person has been treated before infection, establishment of infection will be prevented, or if an infected person is treated before the onset of clinical AIDS symptoms, then disease symptoms should be substantially prevented.

As used herein, a toxin gene encodes a cytotoxic protein active in target cells. In the present case a toxin gene is specifically exemplified by a DT-A coding sequence which differs somewhat from the wild-type DT-A coding sequence, as described in Example 1. This variant DT-A sequence appears to be fully active, and, thus, functionally equivalent to the wild-type DT-A sequence. The term "toxin gene" also encompasses toxin coding sequences which have attenuated activity as compared with the wild-type DT-A, e.g. the tox176 attenuated coding sequence. The skilled artisan will understand that a wild-type DT-A coding sequence can be used in the present invention, and that other toxin genes which have similar fast action for stopping cellular processes leading to viral reproduction can be substituted for the DT-A toxins of the present invention.

An HIV-regulated chimeric toxin gene of the present invention is selectively expressed in the presence of the HIV Tat and Rev proteins. HIV regulatory control is provided by HIV LTR sequences placed upstream of the toxin coding sequence and by HIV-1 env sequences comprising the crs sequence and RRE placed downstream of the toxin coding sequence. In the HIV-regulated chimeric toxin gene, basal expression (in the absence of Tat and Rev) must be sufficiently low so that cell killing does not occur. Lethal amounts of toxin are synthesized when the cell containing the HIV-regulated chimeric toxin gene is infected with HIV and Tat and Rev are produced (or when expressible HIV Tat and Rev protein genes are introduced).

An HIV-regulated chimeric luciferase gene of the present invention encodes enzymatically active luciferase, and is regulated in the same manner as the HIV-regulated chimeric toxin gene described above.

As used herein, the term "selective killing" refers to killing of a target cell but not a non-target cell, even if both types of cells are present in a mixture, as in cell culture or if both types of cells are present in a human patient, and is mediated by an HIV-regulated chimeric toxin gene. In the context of the present application, a target cell is one which has been infected with HIV or one which becomes infected with HIV. A non-target cell as used herein is a cell which is not infected with HIV. More generally, target cells contain the HIV Tat and Rev proteins which will activate the lethal synthesis of an HIV-regulated chimeric toxin gene. The natural functions of the non-target cell should not be significantly affected by the presence of an HIV-regulated chimeric toxin gene.

The "HIV trans-acting factors" of the present invention are those soluble proteins which mediate regulation of gene expression by interacting with HIV cis-acting regulatory sequences. As specifically exemplified herein, the HIV Tat and Rev proteins interact with the TAR and RRE cis-acting sequence elements so as to activate the expression of the associated coding sequence. The art understands that there will be differences among HIV strains and that there will be variations in regulatory protein sequences and cis-acting regulatory sequences, which do not result in a change in function. It is also understood that the skilled artisan can make modifications to naturally occurring amino acid or nucleotide sequences without significantly affecting function; the art knows how to test modified or naturally occurring variant sequences and proteins for maintenance of function. All naturally occurring and man-made variant sequences of HIV regulatory sequences and factors which mediate selective gene expression as described herein are encompassed by the description and claims. Selective gene expression requires that basal expression (in the absence of HIV trans-acting factors) be sufficiently low so as not to be lethal and that expression of an HIV-regulated toxin coding sequence in the presence of HIV trans-acting factors in a cell be sufficiently high to allow for killing of that cell.

An "HIV-infectible cell," as used herein, is a cell which is capable of being infected by HIV. Generally, HIV-infectible cells are recognized by the presence of the CD4 surface glycoprotein, which serves as the receptor for HIV in human T4 cells (see, e.g., Maddon et al. (1985) Cell 42:93–104).

The "HIV cis-acting regulatory sequences" of the present invention are those which confer regulatable gene expression to a coding sequence associated with them. The HIV cis-acting regulatory sequences of the present invention include the TAR element, which mediates activation of downstream genes in the presence of the HIV Tat protein, the RRE which down-regulates expression of associated gene expression in the absence of the Rev protein, and the crs sequence, which also down-regulates associated gene expression. Preferably, the HIV cis-acting regulatory sequences will be placed in orientations, distances and positions relative to the regulated gene which are similar to natural positions, distances and orientations relative to natural regulated genes. The HIV TAR, RRE and crs sequences are known to the art.

It is further understood that the art may discover other regulatory sequences and activating factors to be added to an HIV-regulated chimeric toxin gene, which can further increase selectivity of associated gene expression. The skilled artisan can also add additional known regulatory sequence elements to mediate inducible gene expression, such as a regulatory sequence responding to an environmental signal such as heat, cold or a chemical compound.

As used herein, "stable transformation" of an HIV-regulated chimeric toxin gene means that the chimeric toxin gene is maintained in the cell into which it has been introduced for a sufficient time to mediate lethal synthesis of the toxin gene if and when HIV infection of that cell should occur, and maintenance of the chimeric gene will be such that HIV-dependent regulation remains intact. Basal expression will be sufficiently low (or absent) so that toxin gene-dependent killing of the cell will not occur in the absence of the HIV Tat and Rev proteins.

In developing the targeted expression of DT-A as a gene therapy approach to AIDS, an important goal is to eradicate any leaky toxin gene expression. Further reduction of basal expression of DT-A may be obtainable by utilizing mutations in the promoter region (Nabel and Baltimore (1987) Nature 326:711–713) or less active mutants of DT-A (Maxwell et al. (1987) supra; Breitman et al. (1990) Mol. Cell Biol. 10:474–479). The chimeric toxin genes of the present invention show significant selectivity for killing target cells, but not non-target cells. The HIV genome provides other regulatory systems (reviewed in Jones et al. (1988) Genes & Devel. 2:1101–1114; Garcia et al. (1989) EMBO J. 8:765–778) which could be exploited to increase the specificity of expression and trans-activation level of a toxin gene. Ultimately, the applicability of regulated DT-A expression in therapy will depend not only on obtaining very stringent regulation (as has been achieved in vivo utilizing tissue-specific promoters in transgenic mice, (Breitman et al. (1987) supra; Palmiter et al. (1987) supra), but also on the availability of a gene therapy protocol to introduce the DT-A construct, e.g., by retroviral transduction (Eglitis and Anderson (1988) BioTechniques 6:608–614; Miller and Rosman (1989) BioTechniques 7:980–984), into a patient's lymphocytes, macrophages, glial and/or marrow stem cells.

The ability to kill HIV-infected cells specifically at an early stage in the viral infectious cycle will provide an efficient means of blocking the spread of infectious virus. This can be achieved by the introduction of a gene encoding a lethal product, linked with regulatory elements that respond specifically to viral trans-activating proteins. For this purpose, we use the gene encoding the A fragment of diphtheria toxin, which potently inhibits protein synthesis by enzymatically inactivating elongation factor 2 (Pappenheimer (1977) supra). The possible use of the poliovirus 2A protein as an alternative lethal product has also been suggested (Sun and Baltimore (1989) supra).

The DT-A gene has been shown capable of ablating specific cell populations in mice, demonstrating the feasibility of imposing stringent regulation in vivo on the expression of a potent toxin. The tat and rev genes of HIV, both essential for productive infection, encode trans-acting proteins which strongly enhance the cytoplasmic accumulation of viral mRNAs (Malim et al. (1989) supra; Cochrane et al. (1990) supra). Both products are required for the abundant accumulation of the unspliced and singly spliced mRNAs that encode viral structural proteins, and expression of Rev may be viewed as a switch promoting the transition from an early or latent phase of the viral cycle to the late, productive phase (Daefler et al. (1990) Proc. Natl. Acad. Sci. USA 87:4571). As with other heterologous genes (Tong-Starksen et al. (1987) supra; Felber and Pavlakis (1987) supra), we have shown in transient transfection experiments that the expression of DT-A can be placed under the control of Tat and Rev. This was achieved using a plasmid, pTHA43, in which the DT-A coding sequence was placed downstream of the HIV-1 LTR and upstream of a portion of the env region containing negative regulatory sequences (crs) and the Rev response element (RRE). (See FIG. 1.) The results reported here show that this regulation can be maintained when the pTHA43 transcription unit is integrated into the DNA of stable transformants. Furthermore, evidence is presented showing that such transformants are substantially impaired in the ability to generate virus from a transfected HIV-1 proviral clone.

We have demonstrated that both luciferase and DT-A expression can be regulated by the HIV-1 trans-acting proteins Tat and Rev in transient transfection experiments. This was achieved with plasmids pLUCA43 and pTHA43, in which luciferase or DT-A coding sequences were placed downstream and under the regulatory control of the HIV LTR. Basal expression from these constructs was dramatically reduced (50-fold, for pLUCA43) by the inclusion of negative regulatory (crs) sequences and the Rev response element (RRE) from the HIV genome in the 3' untranslated regions. Additionally, relative trans-activation was increased by the inclusion of these sequences. Both Tat and Rev were required for maximal expression, resulting in 85-fold trans-activation for pLUCA43 and, for pTHA43, inhibition of luciferase expression from 5-30% of the control, depending on the co-transfected luc reporter. The use of the NFK-B mutation contained in env sequence comprising nucleotides 5925-8608 gives very low basal expression and allows significant trans-activation (data not shown).

Several possibilities could explain the relatively greater trans-activation of pLUCA43, as compared to pTHA43, by Tat and Rev. First, expression from the two plasmids was measured directly for pLUCA43, but indirectly for pTHA43 using a transient co-transfection assay (Maxwell et al. (1986)). The indirect assay allowed the detection of DT-A expression in the relatively small percentage of cells which take up DNA in transfection experiments. Due to the high cellular lethality of DT-A, levels of DT-A in transfected cells are very low, and therefore difficult to measure directly. Experiments using the polymerase chain reaction (PCR) should provide a sensitive, quantitative method to directly measure DT-A transcriptional expression in transfected cells. Secondly, the HIV-regulated gene itself appeared to influence both basal expression and relative trans-activation, as significant differences in these parameters were noted in a comparison of HIV-regulated luciferase, DT-A and CAT expression.

HeLa cells with stably integrated pLUCA43 (individual, or pooled clones) showed similar trans-activation of luciferase expression to that observed in the transient transfection assays. Thus, low basal expression and high relative trans-activation levels were maintained upon integration of the HIV-regulated construct. Analogous cell lines stably integrated with pTHA43 have been generated; the demonstration that such cell lines are impaired for HIV production is an important step in the development of toxin gene therapy for AIDS.

In alternative approaches targeting gene expression to HIV-infected cells, genes encoding poliovirus 2A protein (Sun and Baltimore (1989) Proc. Natl. Acad. Sci. USA 86:2143-2146) or L2-interferon (Bednarik et al. (1989) Proc. Natl. Acad. Sci. USA 86:4958-4962) have been placed under control of the HIV LTR. Both these constructs were activated by Tat in isolated stable cell lines. However, these studies did not explicitly incorporate the additional control by the Rev protein as described herein. HIV-regulated expression of a herpes thymidine kinase gene from an adenovirus vector has been proposed as a means of targeting drug-dependent toxicity to HIV-infected cells (e.g., Venkatesh et al. (1990) Proc. Natl. Acad. Sci. USA 87:8746-8750). In that report, an attempt to impose Rev control met with limited success, possibly because of the use of more limited sequences from the env region than those employed herein. Other investigators have described the targeting of protein toxins to HIV-infected cells via the CD4 molecule (Chaudhary et al. (1988) Nature 335:369-379; Till et al. (1988) Proc. Natl. Acad. Sci. USA 86:1987-1991) or anti-gp41 antibodies (Till et al. (1989) supra) which bind the HIV envelope protein expressed on the surfaces of infected cells. Targeting entry of a chimeric toxin gene to particular cell types, such as in liposome-mediated delivery (reviewed in Kirsh et al. (1987) Ann. NY Acad. Sci. 507:141-154), could be used in conjunction with specifically regulated expression to increase the selectivity of cell killing WO 90/07936 and WO 90/10015, also present strategies for delivering toxic effector genes and toxin moieties to HIV-infected cells.

The generation of a retrovirus vector to deliver the HIV-regulated DT-A gene (or an attenuated derivative such as tox176) provides the means for stable integration in cell lines for in vitro studies and ultimately the means for introduction and stable integration of a HIV-regulated toxin gene of the present invention in a human for AIDS prophylaxis or therapy.

In the present study, individual clones of HeLa cells which had integrated pTHA43 generate 50-96% less secreted p24 antigen than control cells, following transfection with an HIV provirus (Table 1). Although the extent of this decrease varied among clones, we also observed that, for a given clone, greater inhibition of p24 production occurred when the cells were transfected with less proviral DNA (2 μg versus 5 μg). Because of the large number of viral genomes entering a cell by DNA transfection, these experiments may underestimate the efficiency with which the production of viral structural proteins would be inhibited in a genuine infection. Work is in progress on the introduction of pTHA43 into HIV-susceptible, CD4-positive cells in order to investigate the ability of this construct to inhibit the replication of HIV introduced by infection.

Use of PCR allowed the detection of the DT-A sequence in total cytoplasmic RNA in the HeLa (pTHA43) transformants, even in the absence of induction by transformation with Tat and Rev expression plasmids. The significance of this observation is at present unclear. It is possible that the cells are able to tolerate a minimal basal level of DT-A expression which is detectable due to the extremely high sensitivity of the PCR. Alternatively, cells within clonal populations might spontaneously express the integrated DT-A at low frequency, presumably with lethal consequences for these cells. This possibility would be consistent with our observation of a tendency for the cell lines to show increased ability to allow pLUCA43 trans-activation as the number of passages in culture increased. Integration of constructs such as pTHA43 or analogous recombinant retroviruses can be maintained, without expression, for long enough periods to be therapeutically useful, e.g., following transduction of bone marrow cells and autologous reimplantation. The skilled artisan will recognize what, if any, modifications in the chimeric genes or vectors are required. For example, if such instability presents a serious problem due to basal toxin expression, the use of an attenuated DT-A mutant such as tox176 instead of the wild-type should improve stability by allowing minimal basal expression to be tolerated. Similarly, modifications of cis-acting regulatory sequences can be made to decrease basal expression, and thus improve selectivity of killing and genetic stability, as understood in the art.

In general, the greater the selectivity for killing HIV-infected cells, but not uninfected cells, the more desirable the HIV-regulated chimeric toxin gene. However, it is understood that the particular application for which such an HIV-regulated chimeric toxin gene will determine the requisite levels of selectivity and/or basal expression.

Deployment of a toxin gene for AIDS therapy, like all currently conceived gene therapy requires an efficient means of introducing the gene constructs into substantial numbers of target cells. Retroviral vectors currently offer the best promise for efficient delivery (Gilboa et al. (1986) BioTechniques 4:504; Miller, A.D. (1990) Blood 76:22)). Recombinant retroviruses can be generated containing the transcription unit from pTHA43. Successful production of such vectors without toxicity to the packaging cells (Miller and Rosman (1989) BioTechniques 7:980) will provide additional assurance that basal expression has been reduced to tolerable levels. Description of retroviral vectors is also given in WO 90/07936, which is incorporated by reference herein.

The concept of intracellular immunization as proposed by Baltimore (1988) supra, involves use of gene transfer to render cells refractory to a viral infection, without toxicity to the cells. Implicit in this concept is the necessity for sustained expression of a product inhibitory to viral replication, probably over an extended period. Substantial expression levels would also be required for certain of the proposed HIV inhibitors, such as dominant negative mutants of gag (Trono et al. (1989) supra) or "TAR decoys" (Sullenger et al. (1990) Cell 63:601), possibly associated with detrimental effects on the cells. In contrast, low level, transient activation of the DT-A gene would suffice to rapidly kill any cell initiating the HIV infectious cycle, without permitting the generation of viral progeny. Continuous cell replacement would occur with further HIV-refractory cells derived from the genetically modified stem cell population containing the regulated toxin gene. Eventually, viral clearance should be achieved through the lack of a reservoir of infectible cells capable of replicating the virus.

For AIDS treatment or for prevention of the disease state in an HIV-infected individual, DT-A (or attenuated derivatives such as tox176) genes whose expression is tightly regulated by HIV cis-acting sequences and trans-acting factors can be introduced into target cells by any means known to the art. Such constructs can be introduced using recombinant retroviruses, e.g., according to WO 90/07936, or using recombinant DNA molecules introduced via liposome technology, e.g., as described in U.S. Pat. No. 4,867,976. For prophylaxis in an uninfected individual, for example, an individual at high risk due to employment, sexual conduct or medical condition, such tightly regulated toxin gene derivatives or recombinant molecules may be introduced into target cells, i.e., those which permit HIV infection, e.g., by incorporation of the recombinant DNA molecules in liposomes targeted to CD4-positive cells by incorporation of CD4-specific antibody, as understood in the art.

The sensitivity for the detection of the HIV-regulated luciferase expression and its inhibition by HIV-regulated DT-A will allow the testing of potential therapeutic compositions for their abilities to depress or prevent HIV replication in vitro. If HIV replication, and therefore, expression of the positive regulators Tat and Rev, is depressed, then there will be a lower activation of both luciferase and DT-A in cells containing both as HIV-regulated genes. Protein synthesis will not be inhibited in cells not expressing DT-A, so appropriate manipulation of incubation time after HIV infection and prior to assay for luciferase activity will allow the skilled artisan to distinguish failure to induce from killing by DT-A. For safety, serially-noninfectious mutants of HIV, known to the art, are preferably used in such assays. Alternatively the skilled artisan can monitor whether protein synthesis was inhibited, e.g., measuring incorporation of radioactive amino acid(s) into protein (as TCA-insoluble material). The skilled artisan will also understand that Tat and Rev proteins can be detected in a cell also bearing an HIV-regulated luciferase gene via an increase in luciferase activity.

An assay of this nature might also be adapted for diagnostic purposes. HIV-infectible cells stably transformed with an HIV-regulated luciferase gene as described herein would be induced to produce luciferase (and light under appropriate assay conditions) if infected with HIV, e.g., from a biological sample such as blood containing HIV. It will be understood by the skilled artisan how to modify the assay parameters to generate a valid assay method.

This invention is illustrated by the following examples, which are not to be construed in any way as imposing limitations on the scope thereof. It is understood that resort can be made to various other embodiments, modifications, alternatives and equivalents of the procedures materials and techniques specifically described which, after reading the description herein, may suggest themselves to those skilled in the art without departing from the spirit of the present invention and/or the scope of the appended claims.

The invention is explained in more detail in the following non-limiting examples. However, these examples should not be construed to limit the scope of the invention thereto and are to be understood merely for the purpose of illustration.

All of the references cited throughout the present Specification are hereby incorporated by reference, in their entirety.

EXAMPLE 1

Plasmid Construction pTHA41, in which the HIV-1 LTR regulatory is just 5′ to DT-A (FIG. 1), was constructed by isolating a 247 base pair XhoI-HindIII fragment containing sequences −167 to +80 of the HIV-1 LTR. This fragment includes the Tat-responsive element, TAR, as well as other regulatory sequences (reviewed in Jones et al. (1988) supra; Garcia et al. (1989) supra). The fragment was made blunt-ended by filling in using Klenow DNA polymerase, and it was then ligated into the SmaI site of pTHA7, a previously described promoterless plasmid (Maxwell et al. (1989) supra) derived from our prototype DT-A expression plasmid, pTH1 (Maxwell et al. (1986)). The DT-A coding sequence of pTH1 and derivatives varied from the wild-type DT-A gene by 2 codons at the amino terminus and an additional 24 codons at the carboxy terminus (Errata (Aug 10, 1990) Cell 62:facing page 608). The modifications to the DT-A sequence do not appear to interfere with DT-A activity. pLUCA41, pTHA42, pLUCA43, pTHA43 and pTHA44 (FIG. 1) were derived from pTHA41. The "A" in this series of plasmids refers to the "A trimer", a trimerized version of the simian virus 40 (SV40) polyadenylation signal which prevents expression of spurious plasmid-initiated transcripts (Maxwell et al. (1989) supra). A DT-A frameshift mutant of pTHA41, designated pTHA42, was constructed for use as "filler" DNA to ensure that all electroporation pulses were with the same amount of HIV LTR-containing DNA. pTHA42 was generated from pTHA41 by filling in an AccI site within the DT-A gene, about 100 nucleotides from the 5' end. pLUCA41 was constructed by substituting a HindIII/ApaI fragment containing the coding sequence for luciferase (together with downstream processing signals from SV40) from the plasmid pSV2A.L-A.Δ5' for the corresponding DT-A-containing sequence in pTHA41. pSV2A.L-A.Δ5' (subsequently designated pSV2A-LUC), was supplied by S. Subramani, as was pRSVL, expressing luciferase under the control of the Rous sarcoma virus LTR (de Wet et al. (1987) Mol. Cell Biol. 7:725-737).

To construct pTHA43 and pLUCA43, a 2683 base pair KpnI fragment, containing nucleotides 5925-8608 of the HIV-1 genome, was isolated from plasmid pIIIAR (Rosen et al. (1988) supra). An intermediate plasmid, pUC18env, was constructed by inserting this sequence into the KpnI site of pUC18. A second intermediate plasmid, pTHA41Dr, was constructed which removed the SV40 small t intron from pTHA41. To generate pTHA41Dr, pIBI30DT-A was first made by inserting a DraI fragment from pTH7 (Maxwell et al. (1989) supra) containing the DT-A gene minus SV40 sequences into the polylinker region of pIBI30DT-A as an NcoI-ApaI fragment which was then cloned into pTHA41 to generate pTHA41Dr, lacking both the SV40 small t intron and polyadenylation signal. During the construction of pTHA41Dr, a SalI site from the polylinker region of PIBI30 was inserted just downstream of the DT-A gene. A SalI-EcoRI fragment from pUC18env (see above), containing the HIV-1 sequences was then inserted into the 3' untranslated region of SalI+EcoRI digested pTHA41Dr to generate pTHA43. pLUCA43 was derived from pTHA43 by inserting a HindIII+XmaI fragment from pJD207 (de Wet et al. (1987) supra), containing the luc cDNA, into pTHA43 digested with SphI+XmaI. This ligation was performed after blunt ending the HindIII and SphI sites of pJD207 and pTHA43, using Klenow and T4 DNA polymerases, respectively, in the presence of nucleoside triphosphates. Both pLUCA43 and pTHA43 are presumed to use the A trimer for polyadenylation of transcripts. pTHA44, a DT-A frameshift mutant of pTHA43, was constructed as described for pTHA42, filling in and re-ligating at the AccI site within the DT-A gene. pTHA41 and pTHA43 are predicted to encode DT-A proteins with C-terminal extensions of 24 and 25 amino acids, respectively, beyond the natural terminus of DT-A; the first 22 of these amino acids are identical, as are the N-termini, which differ from authentic DT-A by 3 amino acids (Maxwell et al. (1989) in Gene Transfer and Gene Therapy, Alan R. Liss, Inc., New York, pp. 189-264). Plasmids pH3tat and pH3art are expression plasmids for HIV-1 proteins Tat and Rev, respectively (Rosen et al. (1988) supra). Both plasmids have the HIV-1 LTR (sequences −167 to +80) as a promoter. HIV-1 sequences are derived from strain HTLV-III (Arya et al. (1985) supra; Fisher et al. (1985) Nature 316:262-265).

The expression plasmids for Tat and Rev, pH3tat and pH3art (Rosen et al. (1988) supra), utilize the HIV-1 promoter. The HIV proviral clone, HXBΔBgl, was derived from HXB2 (Sodroski et al. (1985) supra) by deletion of 500 base pairs between two BglII sites in the env region; HXBΔBgl was a gift from Dr. E. Terwilliger.

EXAMPLE 2

Transfections by Electroporation and Transient Assays

Cells were transfected using a BioRad Gene Pulser with capacitance extender as previously described (Maxwell and Maxwell (1988) DNA 7:557-562). All cell types were grown in Opti-MEM medium (Gibco) with 3.8% fetal bovine serum in Falcon T-75 flasks, and were harvested and resuspended in Opti-MEM with 10% fetal bovine serum for the electroporation pulse. HeLa cells were grown to about 80% confluence and were suspended at $2-4 \times 10^7$ cell/ml to pulse; Jurkat and EL-4 cells (human and murine T cell lines, respectively) were grown to about $1 \times 10^6$ cells/ml and were suspended at $0.5-1 \times 10^8$ cells/ml to pulse; and 3T3 cells were grown to about 80% confluence and were suspended at $5 \times 10^6$ cells/ml to pulse. Pulses were performed in 0.1 ml volumes in Biorad cuvettes with the amounts of DNA indicated. Gene Pulser settings were 220 volts (for HeLa), 250 volts (for Jurkat), 280 volts (for 3T3) or 290 volts (for EL-4), with a capacitance of 250 μfarad, yielding time constants of 25-30 msec. Transient expression of luciferase was measured in lysates prepared 11-21 hours after the pulse. DT-A activity was measured indirectly by its inhibition, presumably at the translational level, of luciferase expression from co-transfected pSV2A-LUC or pLUCA43. Cell harvests, luciferase assays and Biorad protein assays were performed as described (Maxwell and Maxwell (1988) supra), and light units (LUs) measured were corrected to 100 μg of protein. The results are presented in FIG. 3.

EXAMPLE 3

Isolation of Stably Transformed HeLa Cells Expressing an HIV-regulated Luciferase Gene Cells were co-transfected by electroporation (as above) with plasmids pLUCA43 and pSV2-327neo, a modified version of the expression plasmid pSV2neo (Southern and Berg (1982) supra). Selection for drug-resistant cells was in 400 μg/ml G418 (Gibco), added fresh every 3-5 days for approximately two weeks. G418-resistant cells were either cloned or maintained as a pooled population, and were assayed for luciferase expression with or without transient transfection of pH3tat and/or pH3art.

HeLa cells were co-transfected by electroporation, using a BioRad Gene Pulser with capacitance extender as previously described (Maxwell and Maxwell (1988) supra), with either plasmids pTHA43 or pTHA44 and pSV2-327neo, a modified version of the expression plasmid pSV2neo (Southern and Berg (1982) supra). Cells were selected in G418 as described above, and were either maintained as pooled populations of about 350 clones (for pTHA43 and pTHA44), or as individual clones in 24-well plates after picking colonies using sterile cotton swabs (for pTHA43 only). The pooled populations, or expanded clones, were assayed for DT-A expression using the previously described transient co-transfection assay (Maxwell et al. (1986) supra). Luciferase expression was measured 12-20 hours after transfection of pLUCA43+pH3tat+pH3art (2.0-2.5 $\mu$g each). Low luciferase expression could arise by the activation of expression of an integrated DT-A gene by Tat and Rev proteins whose synthesis was directed by pH3tat and pH3art. Five of approximately 60 clones assayed exhibited low luciferase expression in the presence of pH3tat and pH3art, and were selected for further analysis.

In some cases, DT antitoxin (Connaught Labs Inc; 62 $\mu$g/$\mu$l), known to inhibit DT-A activity, was added to the cell suspension at 4-8% before electroporation. See FIG. 7 and its description.

EXAMPLE 4

Trans-activation of an HIV-regulated Luciferase Reporter Gene by Tat and Rev

Figure 1:
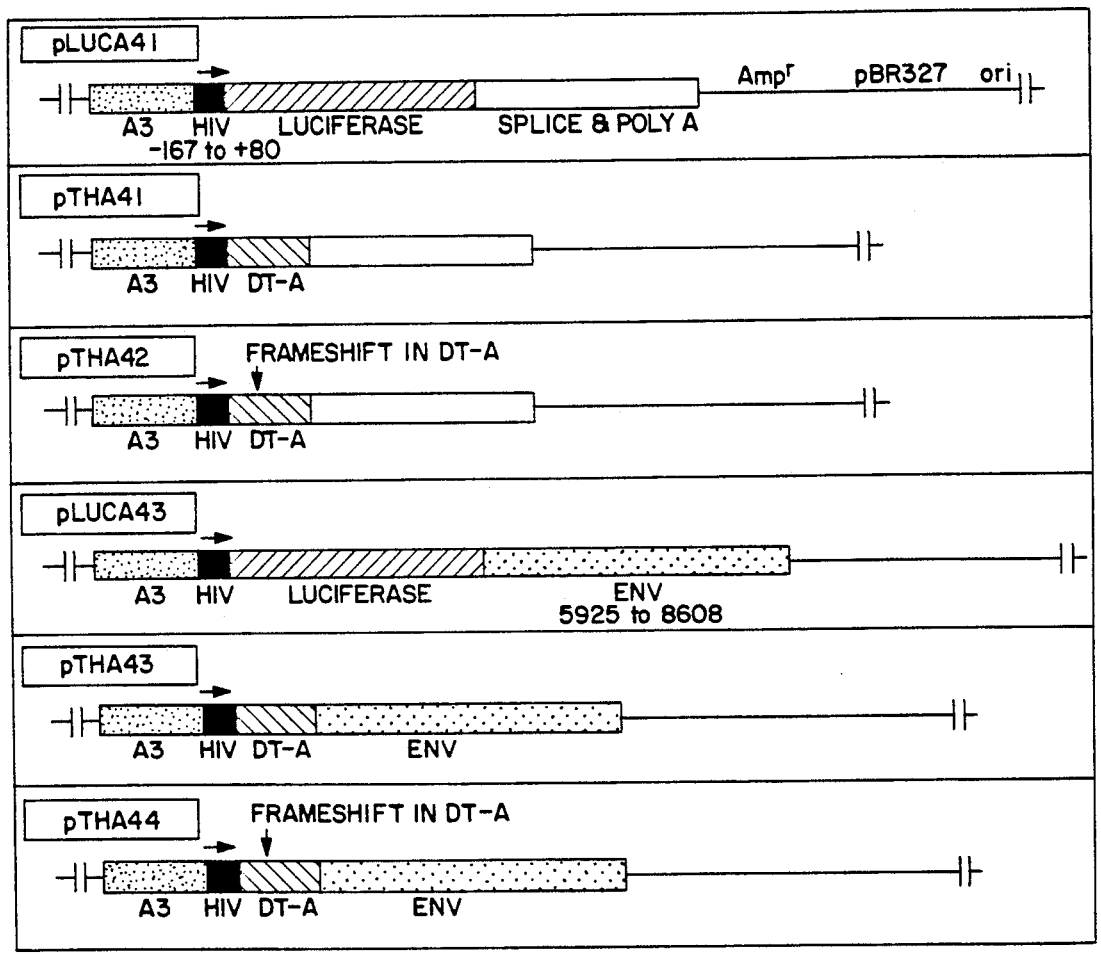
FIG. 1 illustrates the HIV LTR-driven luciferase and DT-A expression plasmids used in transient expression assays. The HIV-1 LTR from nucleotide −167 to +80 is present; this includes the enhancer and the Tat-responsive element (TAR). The luc gene was derived from plasmid pSV2A-LUC (de Wet et al. (1987), and the DT-A gene from pTH7 (Maxwell et al. (1989) Biotechniques 7:276–280). SV40 sequences in pLUCA41, pTHA41 and pTHA42 include the small t intron and the polyadenylation signal. pBR327 sequences include the origin of replication (ori) and the gene conferring ampicillin resistance (amp). The A trimer is a trimerized version of the SV40 polyadenylation signal previously described (Maxwell et al. (1989) supra). The env region in pLUCA43, pTHA43 and pTHA44 contains nucleotides 5925-8608 from the HIV-1 genome and includes sequences which decrease basal expression (crs) and sequences which confer Rev-responsiveness (RRE).
Figure 2:
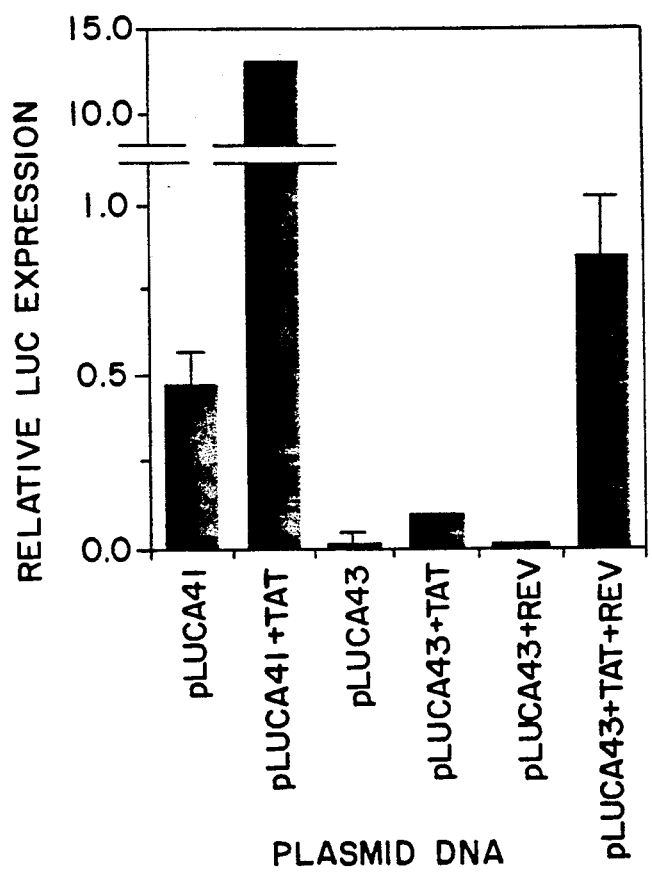
FIG. 2 compares basal and trans-activated luciferase expression levels from plasmids pLUCA41 and pLUCA43 in HeLa cells. Luciferase levels are calculated per 100 μg of protein, and expressed relative to the number of light units obtained when pSV2A-LUC was introduced into parallel samples of cells (normalized to 1.0). Cells were co-transfected with a total of 3.0 μg DNA, which included 1.0 μg of the luc plasmid with or without 1.0 μg each of pH3tat and/or pH3art together with pTHA42 as filler. Cell extracts were prepared for assays 20–21 hours following electroporation. Each bar represents an average from at least two experiments, each assayed with duplicate samples (except for pLUCA43+Tat and pLUCA43+Rev, which were assayed in duplicate once each). Standard deviations are indicated by the error bars except the standard deviation for pLUCA41+Tat, ±4.0 (not indicated as it is off the scale).

Initial experiments aimed at demonstrating trans-activation of an HIV-1 LTR-driven reporter gene used the luc reporter gene described by de Wet et al. (1987) supra. We reasoned that any basal expression of the reporter (that is, expression in the absence of trans-activation) would be easily detected using the highly sensitive luciferase assay. Plasmid pLUCA41 contains the HIV-1 LTR ($-167$ to $+80$) 5' to luc cDNA (FIG. 1). This region of the LTR includes the enhancer and the Tat-responsive element, TAR. FIG. 2 shows the basal and trans-activated expression levels from pLUCA41 in HeLa cells, plotted as a ratio of LUs obtained when an equal amount of pSV2A-LUC (expressing luc from the SV40 promoter) was introduced into parallel samples of cells. Expression from pLUCA41 was increased 28-fold in the presence of pH3tat above a basal expression level which was, however, substantial (almost 50% that obtained with pSV2A-LUC). While this level of trans-activation was encouraging, the high basal expression would be unacceptable for HIV-regulated DT-A expression, where any (leaky) expression would be potentially lethal to cells.

To decrease basal expression, we incorporated negative regulatory (crs) sequences from the env region of the HIV-1 genome into pLUCA41, generating pLUCA43. Sequences between nucleotides 6376 and 7760 of the HIV-1 genome strongly inhibit expression of HIV-1 LTR-driven constructs when included in the 3' untranslated region (Rosen et al. (1988) supra), an effect which is overcome by the HIV-1 gene product Rev. pLUCA43 contains nucleotides 5925-8608 of HIV-1 inserted in the 3' untranslated region downstream of the luc coding sequences (FIG. 1). As shown in FIG. 2, this insertion dramatically decreased basal expression from the HIV-1 LTR sequences. Luciferase expression from pLUCA43 in the absence of trans-activation was 1% of that from the pSV2A-LUC control, a reduction of 50-fold compared to pLUCA41. In the presence of pH3tat and pH3art, pLUCA43 expression was increased 85-fold. Thus, the relative level of trans-activation was substantially higher than that of pLUCA41 (85-fold compared to 28-fold). Both Tat and Rev-expressing plasmids were required for maximal expression of pLUCA43; pH3tat alone resulted in only 10-fold activation compared to basal expression, while pH3art, which expresses Rev, alone did not result in detectable activation. pLUCA41 was completely unresponsive to Rev.

In these experiments, pTHA42 (FIG. 1) was used as filler DNA so that all electroporations were performed with an equivalent amount of HIV LTR-containing DNA. To rule out the possibility that pTHA42 was inhibiting pLUCA43 expression, perhaps by competing for transcription factors, we compared luciferase expression in HeLa cells electroporated with pLUCA43, with or without pTHA42. In each case, the LUs measured were very low, being only about twice background levels. Thus, the low basal expression from pLUCA43 was not attributable to an inhibitory effect of the filler DNA on pLUCA43 luciferase expression.

Luciferase-expressing stable cell lines were generated by co-transfection of HeLa cells with pLUCA43 and pSV2-327neo, an expression plasmid conferring G418 resistance. G418-resistant cells were either cloned or maintained as a pooled population. Table 2 shows the luciferase activity measured in extracts of these cells with or without transient transfection with the Tat and/or Rev expression plasmids. As in the transient assays, luciferase expression in both the HeLa luc19 clone and the pooled population was weakly activated by pH3tat or pH3art alone, and was strongly activated by pH3tat+pH3art together. This demonstrates that a reporter gene stably integrated into a host genome can be stringently controlled by the HIV regulatory proteins Tat and Rev and crs, and serves as a useful paradigm for the isolation of analogous cell lines with a stably integrated HIV-regulated DT-A gene.

EXAMPLE 5

Basal Expression of HIV-regulated DT-A Constructs in Various Cell Types is Significantly Reduced by CRS Sequences in the 3' Untranslated Region Plasmids analogous to pLUCA41 and pLUCA43 were constructed, with the A chain of diphtheria toxin as the HIV-regulated gene instead of luc (FIG. 1). DT-A expression from these plasmids, pTHA41 and pTHA43, was assayed indirectly by its inhibition (presumably at the translational level) of luciferase expression from a cotransfected luc reporter plasmid (pRSVL). Luciferase expression and DT-A expression should therefore be inversely related. FIG. 3, Panel A compares basal expression from plasmids pTHA41 and pTHA43 (the latter contains the negative regulatory HIV crs sequences). The results are expressed as a percentage of the control luciferase activity seen when the luc reporter was transfected into parallel samples of cells in the presence of filler DNA only (pTHA42 as a filler for pTHA41, and pTHA44 as a filler for pTHA43). Basal expression from pTHA43 was substantially reduced compared to that from pTHA41 for all cell types examined. In murine EL-4 T cells, essentially zero basal expression was observed from pTHA43

(FIG. 3 Panel A); this was also true when the amount of pTHA43 included in the electroporation was doubled to 0.4 μg (not shown).

Figure 3A:
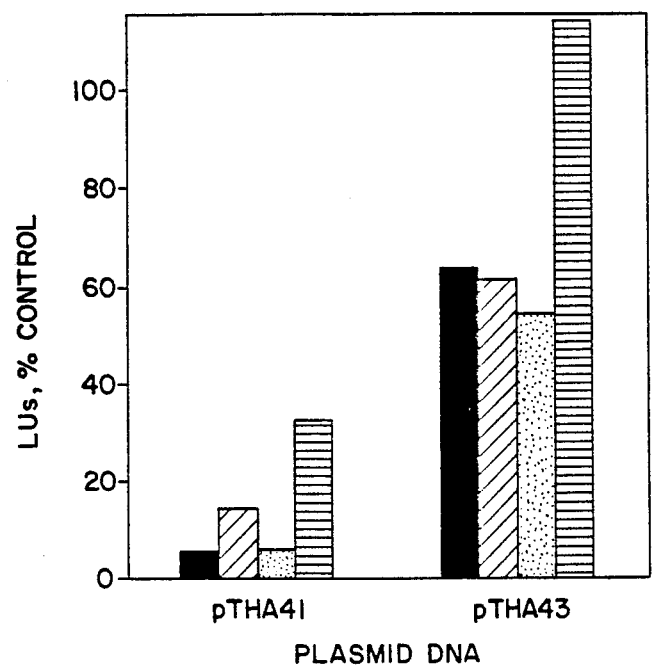
FIG. 3A–3B illustrates expression of HIV-regulated DT-A plasmids in several cell lines. Panel A gives the basal expression of pTHA41 and pTHA43 in HeLa, Jurkat, 3T3 and EL-4 cells. In Panel A, cells were co-transfected with 4 μg of luc reporter (pRSVL) and 0.2 μg of either pTHA42, pTHA41, pTHA44 or pTHA43. Cells were harvested for assays 16 hours following electroporation. Luciferase levels are expressed as a percentage of control: for LUC+pTHA41, the control was LUC+pTHA42; for LUC+pTHA43, the control was LUC+pTHA44. Solid bars, HeLa; diagonally hatched bars, Jurkat; stippled bars, 3T3; horizontally striped bars, EL4. Data with HeLa and Jurkat cells were from two experiments each, performed with duplicate samples. Data with 3T3 and EL4 cells were from one experiment each, performed with duplicate samples.
Figure 3B:
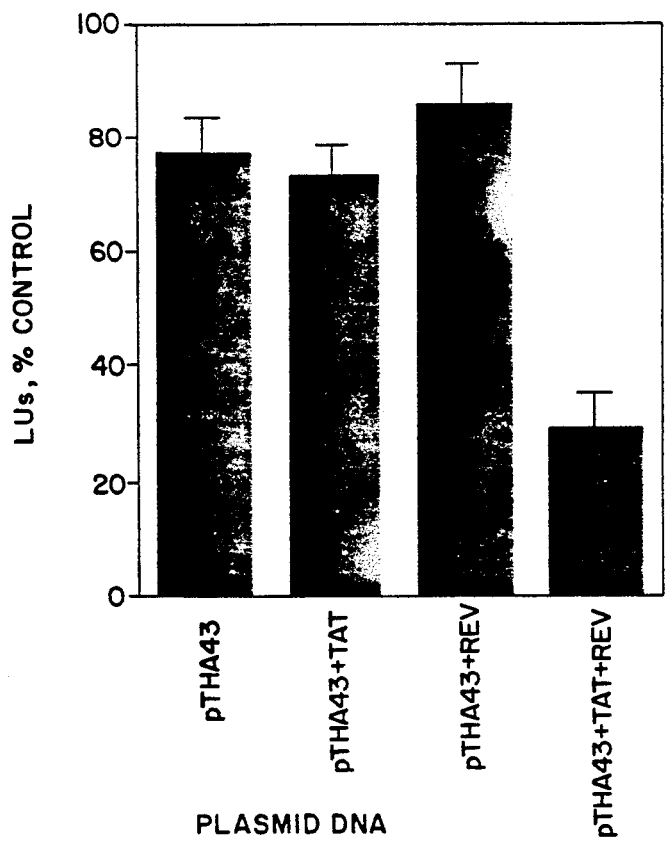

FIG. 3 Panel B shows trans-activation of pTHA43 in HeLa cells using pRSVL as the co-transfected reporter plasmid. In each case, the numbers are expressed as a percentage of pRSVL co-transfected with pTHA44 (as a filler for pTHA43) and also with pH3tat and/or pH3art when included in the corresponding pTHA43-containing samples. As already seen (FIG. 3A), basal expression from pTHA43 in the absence of trans-activation resulted in a slightly decreased level of luciferase expression (78% compared to the pRSVL+pTHA44 control, FIG. 3 Panel B). In the presence of both pH3tat and pH3art, DT-A expression was increased, resulting in a reduction of luciferase activity to 30% of the control. Similar results were obtained for Jurkat and EL-4 cells. The difference between DT-A expression with pTHA43 alone (in the presence of filler pTHA42) to pTHA43+pH3tat+pH3art, was significant at the $p<.001$ level (t test for independent samples). In contrast, the addition of either pH3tat or pH3art alone did not significantly trans-activate DT-A expression from pTHA43 ($p \leq .20$).

While these data indicated significant trans-activation of DT-A expression from pTHA43 by Tat+Rev, the effect was not as dramatic as that seen for luciferase expression from pLUCA43 (FIG. 2). Such a comparison is not straightforward because the assay for DT-A expression is indirect, and the sensitivity is greater for luciferase. Nevertheless, these results suggest that the HIV-regulated gene itself may influence both the basal expression (lower for pLUCA43 than pTHA43) and the level of trans-activation (higher for pLUCA43 than pTHA43). Chloramphenicol acetyl transferase (CAT) has been used as an HIV-regulated reporter (Rosen et al. (1988) supra), with nearly undetectable basal expression and >800-fold trans-activation (not shown). This supports the notion that the particular HIV-regulated reporter gene being studied can affect HIV-regulated expression by as yet undefined mechanisms.

Figure 4:
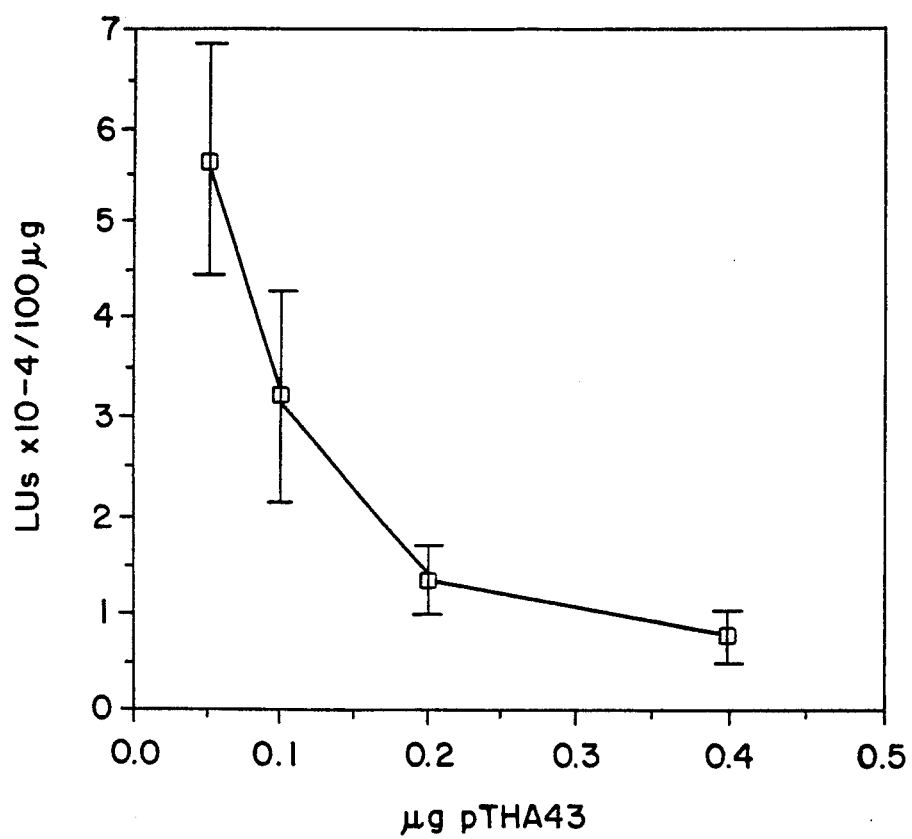
FIG. 4 illustrates the decrease in luciferase expression from pLUCA43 with increasing amounts of co-transfected pTHA43 in HeLa cells. Light units are calculated per 100 μg of protein. 4.0 μg of pLUCA43 was co-transfected into cells with 1.0 μg each of pH3tat and pH3art, and the indicated amount of pTHA43. pTHA42 was used as filler DNA so that all samples contained an equal amount of HIV LTR-containing DNA. Cells were harvested for assays 20 hours following electroporation. Each point is an average from two experiments, each performed with duplicate samples. Standard deviations are indicated by the error bars.

We attempted to increase the sensitivity of detecting DT-A expression from plasmid pTHA43 by using different cotransfected luc reporters. In the dose-response curve shown in FIG. 4, pTHA43+pH3tat+pH3art appeared markedly more inhibitory when pLUCA43 rather than pRSVL (FIG. 3B) was used as a reporter. For comparison, 0.2 μg of pTHA43 resulted in 95% inhibition of luciferase expression from pLUCA43 but only 70% inhibition of luciferase expression from pRSVL. We have also observed greater inhibition by pTHA43 with pLUCA41 as a reporter compared to pRSVL. These results suggest that the use of pRSVL as a reporter in the transient co-transfection assay (FIG. 3) may lead to underestimation the level of DT-A expression.

HeLa cells were transfected with pSV2-327neo, and either the HIV-regulated DT-A plasmid (pTHA43) or the DT-A frameshift mutant plasmid (pTHA44). G418-resistant cells were analyzed, as either pooled populations or expanded clones, for luciferase expression from a reporter plasmid, transfected with or without pH3tat+pH3art. The induction of DT-A expression from an integrated pTHA43 construct by Tat+Rev should result in lower trans-activated luciferase levels compared to controls. pLUCA43, an HIV-regulated luciferase construct, was used as a reporter since we have previously shown that luciferase expression from this plasmid is extremely sensitive to DT-A expression. In the pTHA43 pooled population, luciferase expression in the presence of pH3tat and pH3art (expression plasmids for Tat and Rev, respectively) was only about 60% of that obtained with either the pTHA44 pooled population or with parental HeLa cells. Basal expression from pLUCA43 (in the absence of pH3tat and pH3art) was similar in the cells tested, indicating that impaired ability to express transfected DNA did not account for the observed difference in trans-activated expression. This suggested that a substantial fraction of cells in the pTHA43 pool had integrated the regulated DT-A gene which could be induced by Tat+Rev. As similar numbers of colonies were obtained for the pTHA43 and pTHA44 pools, substantial basal expression of the integrated DT-A construct was not apparent.

Using the same assay as for the pooled populations, five separate clones were identified which showed a much larger reduction in trans-activated luciferase expression, to 3-14% of that observed with control G418-resistant clones lacking the DT-A sequence. These data are shown in FIG. 6. While basal expression levels varied among the positive clones, the amount was insufficient to account for the substantially larger differences in trans-activated expression levels.

If the decreased luciferase expression resulted from activation of DT-A in these clones, then higher luciferase levels should be restored upon inhibition of DT-A activity. DT antitoxin, known to inhibit DT-A activity, was therefore added to the cell suspension just prior to electroporation with pLUCA43+pH3tat+pH3art. The electroporation conditions used allowed uptake of both DNA and proteins from the medium. The data are shown in FIG. 7. The four clones tested showed significant restoration of luciferase expression, with a 2.3 to 6-fold increase compared to the absence of antitoxin. Conversely, HeLa cells and one of the negative clones showed no significant change in luciferase expression upon addition of the antitoxin. This effect was specific for antitoxin, as an "irrelevant" control antiserum (against H. influenzae) gave no rescue of luciferase expression.

EXAMPLE 6

Detection of DT-A Sequences in pTHA43-transformed Cell Lines

PCR analysis was used to demonstrate the presence of DT-A sequences in the five pTHA43 stable cell lines. Oligonucleotide primers hybridizing to DT-A and HIV LTR sequences were chosen so as to amplify bands of ~330 base pairs (containing DT-A sequences) and ~600 base pairs (containing HIV LTR and DT-A sequences).

PCR was performed on DNA and reverse-transcribed RNA isolated from the five putative pTHA43-positive clones selected as described above, and also from several pTHA43-negative, G418-resistant, clones. For DNA-based PCR, $6 \times 10^6$ cells were washed in PBS and lysed in 50 mM tris-HCL (pH 8), 50 mM EDTA (pH 8), 0.5% SDS and 500 μg/ml Proteinase K (Boehringer Mannheim). Cell lysates were kept at 55° C. overnight and then stored at 4° C. PCR was performed with about 60 ng of DNA from the cell lysate in: 50 mM KCl, 10 mM tris-HCl (pH 8.3), 1.5 mM MgCl$_2$, 0.01% gelatin, 0.33 mM dNTPs, 0.04 units/μl of either Taq (Perkin Elmer/Cetus) or VENT (New England Biolabs) polymerases, and 1.67 μM of each primer. Oligonucleotide primers, hybridizing to sequences contained within the first 400 base pairs of DT-A, were selected to amplify a band of ~330 base pairs. In some cases an additional oligonucleotide primer was included which hybridized to sequences −165 to −145 of the HIV LTR; this resulted in amplification of a band of −600 base pairs, containing LTR and DT-A sequences. PCR conditions in either the Perkin Elmer/Cetus Thermal Cycler or the BioTherm oven were: 94° C., 1.5 minutes; 50° C., 2 minutes; 72° C., 1.5 minutes, for 30 cycles. PCR products were detected with ethidium bromide staining following electrophoresis in a 3% NuSieve GTG (FMC), 1% agarose gel.

For RNA-based PCR, total cellular RNA was isolated from cells using standard procedures (Maniatis et al. (1982) *Molecular Cloning: A Laboratory Manual*, Cold Spring Harbor Laboratory, Cold Spring Harbor, N.Y.). 2.5 μg of RNA was reverse transcribed in PCR buffer containing 1 mM dithiothreitol, 0.2 mM dNTPs, 0.5–1.0 units/μl RNasin (Promega), $5 \times 10^{-5}$ units/μl oligo dT12–18 primer (Pharmacia), and 100 units/μg Moloney murine leukemia virus reverse transcriptase (BRL). Reverse transcription was performed at 37° C. for two hours; 1/5 of the cDNA was then used for the PCR reaction as described above.

The data with the oligonucleotide primers amplifying the 300 base pair band are shown in FIG. 5 Panel A; all five clones showing decreased pLUCA43 activation, above, were positive for DT-A DNA sequences while 3/3 G418-resistant clones showing normal pLUCA43 activation were negative for DT-A sequences. Similar results were obtained using the primers amplifying the 600 base pair band.

PCR was performed on cDNA, reverse transcribed from total RNA of the five pTHA43 stable clones, isolated with or without prior transfection with pH3tat+pH3art. Additionally, two pTHA43-negative, G418-resistant clones were analyzed. All positive clones showed a DT-A band, by ethidium staining, in the presence or absence of pH3tat+pH3art, but no band was observed in the absence of reverse transcription. The negative control samples showed no DT-A band under any conditions. Data are shown in FIG. 5 Panel B for two positive (43- C21 and -D4) and one negative (43-C3) clones. Thus, DT-A expression could be detected in the positive clones (but not in the negative clones) in the presence or absence of trans-activation. This is conceivably due to the extreme sensitivity of PCR, and may indicate that the conditions used were not quantitative. Thus, if only a very low amount of DT-A was expressed in some of the cells, the band generated may be of equal intensity to that seen if all cells were expressing a high amount of DT-A.

EXAMPLE 7 p24 and Luciferase Assays in HeLa Stable Cell Lines Upon Transfection of an HIV Proviral Clone The five HeLa stable clones (43-A2, -C21, -C2G, -D2 and -D4) were transfected with the HIV provirus, HXBΔBgl. HXBΔBgl encodes the HIV genome with a 500 base pair deletion in the env region; thus, viral particles are produced during one round of replication but are noninfectious due to the absence of the envelope protein. p24 levels resulting from the single round of HIV replication were assayed in the HeLa pTHA43 stable clones, and values were compared to those obtained with either parental HeLa cells, or the pooled population transfected with the DT-A frameshift plasmid, pTHA44. The data are shown in Table 2, with absorbance readings normalized to 40 μl of cell supernatant. All five stable cell lines exhibited substantially lower p24 values than either normal HeLa cells or the pTHA44 pool. Three clones exhibited very low p24 values on both days 1 and 2 (between 3.5–17% of control; clones 43-C21, -D4, and -C2G). The other clones (43-D6 and -A2) had somewhat higher p24 values (although still <50% of control), which also increased between days 1 and 2. The higher p24 values in these clones could be due to the higher amount of provirus transfected into these cells (5 μg vs. 2 μg), which could have resulted in more viral production before the full induction of DT-A compared to the other three clones which exhibited a much more dramatic inhibition of p24.

We also examined the ability of the provirus, HXBΔBgl, to trans-activate luciferase expression from co-transfected pLUCA43. Data are presented in Table 3 for two stable cell lines and parental HeLa cells; basal luciferase expression from pLUCA43 was compared to trans-activated luciferase expression with either HXBΔBgl or pH3tat+pH3art. Trans-activation of luciferase expression (by either HXBΔBgl or pH3tat+pH3art) was very low in the stable clones compared to HeLa cells, and was even undetectable by day 2 in the clone 43-D4. In HeLa cells, the trans-activated luciferase level was several-fold higher with the provirus than with pH3tat+pH3art on day 1; by day 2, however, the trans-activated levels were similar. Both stable cell lines showed a decrease in trans-activated luciferase levels between days 1 and 2, suggesting that expression of the integrated DT-A gene was efficiently induced by both pH3tat+pH3art and the HIV provirus.

p24 assays were performed using an HIV p24 Ag Assay kit (Coulter Immunology) as instructed. 5 to 60 μl of cell supernatant was assayed 24 and 48 hours following transfection of HXBΔBgl. Absorbance was determined using an ELISA microtiter plate reader. As it was determined that the linear range of the assay extended to an absorbance of ~0.7, the color reaction was usually stopped sooner than the 30 minutes indicated in the p24 kit instructions.

EXAMPLE 8

Construction of a HIV-Regulated DT-A Recombinant Retrovirus

An improved N2-based retrovirus vector LNSX has been described by Miller and Rosman (1989) BioTechniques 7:980; the N2 Armentano et al. (1987) J. Virol. 61:1647.

The modifications in LNSX include mutation of the gag start codon and replacement of the upstream region of the vector with the homologous region from Moloney mu. sarcoma virus which does not make glycosylated gag Further modifications include insertion of a unique cloning array downstream to an SV40 early promoter region. This construct eliminates the risk of homologous recombination with endogenous sequences which could generate helper virus, and also yields higher titer viral stocks than previous constructs. LNSX retains the neo gene, so selection for clones which have integrated the retrovirus can be performed in G418. The recombinant DT-A proviruses were constructed, designated LNX-Th43 and LNX-Th43R (corresponding to two opposite orientations), were based on LNSX.

A XhoI linker was inserted in place of the SV40 promoter of LNSX. A XhoI fragment from pTHA43, containing the HIV LTR from −167 to +80, DT-A, and 5925-7325 of the env region of HIV (containing CRS and RRE sequences) was then inserted into the XhoI site of the modified LNSX. Restriction digests were used to identify both orientations of the insert. LNX-Th43, which has the same orientation as the viral promoter, should utilize the polyadenylation signal in the viral 3′ LTR; LNX-Th43R was not specifically provided with a polyadenylation signal.

LNX-Th43 and LNX-Th43R were tested in transient assays. The DT-A retroviral constructs were electroporated into cells along with a luciferase reporter gene (pLUCA43) and pH3tat+pH3art. Expression of DT-A from the retroviral constructs, as measured by inhibition of luciferase expression, was similar to that of the plasmid pTHA43. This data is summarized below for two different amounts of the indicated DT-A construct:

% control LUC expression with:

| μg DT-A construct | pTHA43 | LNX-Th43 | LNX-Th43R |
|---|---|---|---|
| 0.05 | 6 | 23 | 13 |
| 0.2 | 3.6 | 7.1 | 4.9 |

These results show that Tat+Rev dependent expression of the regulated DT-A gene was maintained after insertion into the provirus (in either orientation) at a level comparable with that from the parental plasmid, pTHA43.

TABLE 1

Trans-Activation of Luciferase Expression in HeLa Cells Stably Transformed with pLUCA43

| Plasmid DNA | LUs per 100 μg protein | | Trans-Activation Level* | |
|---|---|---|---|---|
| | HeLa luc19 | Pool | HeLa luc19 | Pool |
| pTHA42 (filler) | 26 | 1,009 | 1 | 1 |
| pH3tat+pTHA42 | 573 | 5,511 | 22 | 5.5 |
| pH3art+pTHA42 | 32 | 2,475 | 1.2 | 2.5 |
| pH3tat+pH3art | 2982 | 34,559 | 115 | 34.3 |

*LUs expressed relative to basal expression (pTHA42 alone).
Cells were electroporated with a total of 5.0 μg DNA (consisting of either 5.0 μg of filler pTHA42; 2.5 μg of pH3tat or pH3art with 2.5 μg pTHA42; or 2.5 μg each pH3tat and pH3art), and were harvested 11-14 hours following electroporation. Each number is an average of duplicate samples from one experiment. "Pool" refers to a pooled population of transformants derived from approximately 600 individual G418 resistant colonies. HeLa luc19 is a cloned transformant.

TABLE 2 p24 levels (absorbance reading) in culture supernatants from pTHA43 stably transformed clones or from HeLa parental cells following transfection with HIV proviral DNA

| Clone | Day 1 (%) | Day 2 (%) |
|---|---|---|
| Experiment 1: | | |
| 43-C21 | .07 (3.5) | .23 (4.2) |
| 43-D4 | .09 (4.9) | .23 (4.2) |
| HeLa | 1.88 | 5.46 |
| Experiment 2: | | |
| 43-D6 | .47 (29) | .59 (50) |
| 43-A2 | .38 (23) | .57 (49) |
| 43-C2G | .17 (10) | .20 (17) |

TABLE 2-continued p24 levels (absorbance reading) in culture supernatants from pTHA43 stably transformed clones or from HeLa parental cells following transfection with HIV proviral DNA

| Clone | Day 1 (%) | Day 2 (%) |
|---|---|---|
| HeLa-pTHA44 pool | 1.64 | 1.17 |

Numbers in parenthesis represent percentages of the corresponding control values obtained with either HeLa cells untransfected (Expt 1) or with a stable HeLa pool transfected with the frameshift DT-A plasmid pTHA44 (Expt 2). Values shown were obtained following transfection of either 2 μg (Expt 1) or 5 μg (Expt 2) of the HIV provirus.

TABLE 3

Luciferase levels (light units × 10⁻³) in pTHA43 stably transformed clones or in HeLa parental cells

| Cell Line | Basal | +pH3tat+pH3art | +HXB B gl |
|---|---|---|---|
| 43-C2 | 1.5; 2.0 | 18.6 (12.3); 9.8 (4.9) | 15.7 (10.4); 4.9 (2.5) |
| 43-D4 | 6.0; 10.0 | 12.6 (2.1); 7.1 (0.71) | 15.5 (2.6); 3.3 (0.33) |
| HeLa | 3.0; 7.3 | 213 (70.3); 943 (129) | 863 (285); 662 (90.8) |

Light units are shown as: day 1; day 2 following electroporation with indicated plasmids: 2.5 μg of pLUCA43 alone (basal), or together with either 2.5 μg each of pH3tat and pH3art or 5.0 μg of HXB B gl. Numbers in parentheses correspond to the ratio of trans-activated/basal levels.

We claim:

1. A method for the selective killing of an HIV-infected cell, said method comprising the step of:
   (a) introducing into said cell a recombinant DNA molecule comprising an HIV-regulated chimeric diphtheria toxin fragment A gene, wherein said diphtheria toxin fragment A gene is expressed under the regulatory control of HIV cis-acting regulatory sequences and trans-acting factors, wherein the expression of said HIV-regulated chimeric diphtheria toxin fragment A gene is activated by HIV trans-acting factors present in said HIV-infected cell, thus killing said HIV-infected cell which has incorporated said recombinant DNA molecule after activation by the HIV trans-acting factors.

2. The method of claim 1 wherein said toxin gene is tox176.

3. The method of claim 1 wherein said HIV trans-acting factors comprise an HIV Tat protein and an HIV Rev protein.

4. The method of claim 1 wherein said HIV cis-acting sequences comprise an HIV TAR element, an HIV RRE element and an HIV crs element.

5. The method of claim 4 wherein said HIV cis-acting sequences comprise nucleotides from −167 to +80 of an HIV LTR positioned upstream of said chimeric toxin gene and further comprising nucleotides 5925-8608 of HIV-1 positioned downstream of said toxin sequence.

6. The method of claim 5 wherein said recombinant molecule is pTHA43.

7. The method of claim 5 wherein said recombinant molecule is one of LNX-Th43 and LNX-Th43R.

8. A method for selective killing of a stably transformed cell line after infection with HIV, wherein said cell line is stably transformed with a recombinant DNA molecule comprising an HIV-regulated chimeric diphtheria toxin fragment A gene, wherein said diphtheria toxin fragment A gene is expressed under the regulatory control of HIV cis-acting regulatory sequences and HIV trans-acting factors, and wherein the expression of said chimeric diphtheria toxin fragment A gene is activated in the presence of HIV trans-acting factors, whereby when said cell line is infected with HIV, HIV trans-acting factors activate the expression of said chimeric diphtheria toxin fragment A gene, thus killing the HIV-infected, stably transformed cell.

9. The method of claim 8 wherein said toxin gene is tox176.

10. The method of claim 8 wherein said HIV trans-acting factors comprises an HIV Tat protein and an HIV Rev protein.

11. The method of claim 8 wherein said cis-acting sequences comprise an HIV TAR element, an HIV RRE element and an HIV-1 crs element.

12. The method of claim 11 wherein said HIV cis-acting sequences comprise nucleotides from −167 to +80 of an HIV LTR positioned upstream of said toxin gene and further comprising nucleotides 5925–8608 of HIV-1 positioned downstream of said toxin coding sequence.

13. The method of claim 12 wherein said recombinant DNA molecule is pTHA43.

14. The method of claim 12 wherein said recombinant DNA molecule is one of LNX-Th43 and LNX-Th43R.

* * * * *